(12) United States Patent
Shimada et al.

(10) Patent No.: US 8,915,900 B2
(45) Date of Patent: Dec. 23, 2014

(54) DISPOSABLE PANTS-TYPE DIAPER

(75) Inventors: Takaaki Shimada, Kagawa (JP); Akiko Yagi, Kagawa (JP); Hideaki Maki, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 584 days.

(21) Appl. No.: 12/742,729

(22) PCT Filed: Aug. 14, 2008

(86) PCT No.: PCT/JP2008/064595
§ 371 (c)(1),
(2), (4) Date: Aug. 23, 2010

(87) PCT Pub. No.: WO2009/063666
PCT Pub. Date: May 22, 2009

(65) Prior Publication Data
US 2011/0022019 A1    Jan. 27, 2011

(30) Foreign Application Priority Data
Nov. 15, 2007  (JP) ................................ 2007-297301

(51) Int. Cl.
| A61F 13/15 | (2006.01) |
| A61F 13/20 | (2006.01) |
| A61F 13/49 | (2006.01) |
| A61F 13/494 | (2006.01) |

(52) U.S. Cl.
CPC ..... *A61F 13/49014* (2013.01); *A61F 13/49011* (2013.01); *A61F 13/49466* (2013.01); *A61F 2013/49028* (2013.01)
USPC ............. 604/385.27; 604/385.29; 604/385.24

(58) Field of Classification Search
USPC .............. 604/385.01, 385.101, 385.24–385.3
See application file for complete search history.

(56) References Cited

U.S. PATENT DOCUMENTS

| 5,554,145 A | * | 9/1996 | Roe et al. .................... 604/385.3 |
| 5,569,232 A | * | 10/1996 | Roe et al. .................... 604/385.3 |
| 5,749,866 A | * | 5/1998 | Roe et al. .................. 604/385.24 |
| 5,941,865 A | | 8/1999 | Otsubo et al. |
| 8,221,376 B2 | * | 7/2012 | Otsubo et al. ............ 604/385.27 |
| 2002/0045877 A1 | * | 4/2002 | Shimada et al. ......... 604/385.29 |
| 2002/0068919 A1 | * | 6/2002 | Shinohara et al. ....... 604/385.27 |

(Continued)

FOREIGN PATENT DOCUMENTS

| JP | 2002-065733 | 3/2002 |
| JP | 2002-248127 | 9/2002 |

(Continued)

OTHER PUBLICATIONS

International Search Report from corresponding PCT application No. PCT/JP2008/064595, dated Nov. 25, 2008, 4 pages.

*Primary Examiner* — Michele M Kidwell
(74) *Attorney, Agent, or Firm* — Brinks Gilson & Lione

(57) ABSTRACT

A disposable diaper having front and rear waist regions that comprise an upper elasticized region extending in a vicinity of a waist-opening periphery, lower elasticized regions, intermediate elasticized region extending between the upper elasticized region and the lower elasticized regions and outside longitudinally opposite ends of a liquid-absorbent structure. At least in the front waist region of the front and rear waist regions, there is a non-elasticized region opposed to a central zone of a liquid-absorbent core wherein a tensile stress of the intermediate elasticized region is lower than a tensile stress of the upper elasticized region.

16 Claims, 4 Drawing Sheets

(56) References Cited

U.S. PATENT DOCUMENTS

2003/0199841 A1* 10/2003 Ashton et al. ............ 604/385.01
2004/0243083 A1* 12/2004 Matsuda et al. ......... 604/385.01
2005/0010188 A1*  1/2005 Glaug et al. .................. 604/396
2005/0080394 A1*  4/2005 Otsubo et al. ............ 604/385.27
2007/0233034 A1* 10/2007 Hildeberg et al. ....... 604/385.24

FOREIGN PATENT DOCUMENTS

| JP | 2004-049765 | 2/2004 |
| JP | 2005-334676 | 12/2005 |
| JP | 2007-082890 | 4/2007 |

\* cited by examiner

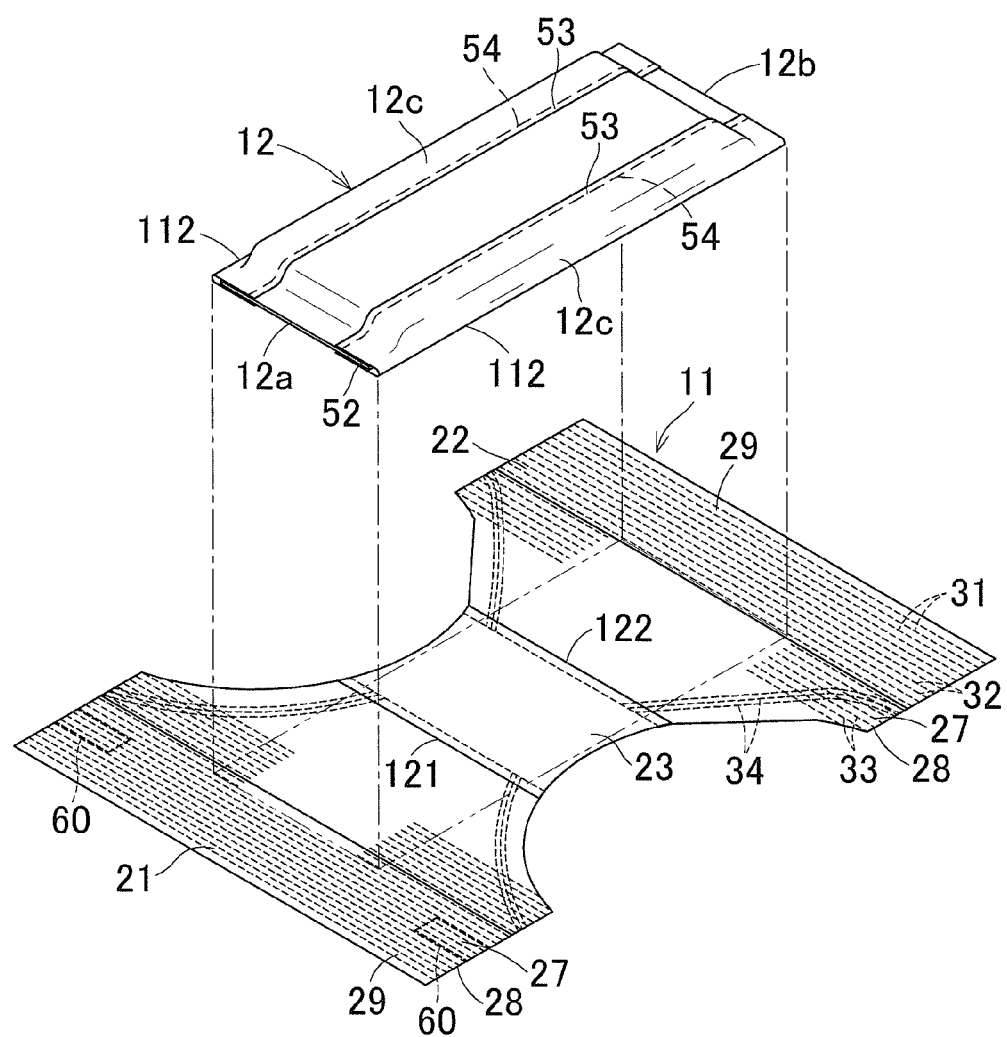

DISPOSABLE PANTS-TYPE DIAPER

RELATED APPLICATION

This application is a 35 U.S.C. §371 national phase filing of International Patent Application No. PCT/JP2008/064596, filed Aug. 14, 2008, through which and to which priority is claimed under 35 U.S.C. §119 to Japanese Patent Application No. 2007-297301, filed Nov.15, 2007.

TECHNICAL FIELD

The present invention relates to a disposable diaper and particularly to a disposable diaper having a good fit to the wearer's body.

RELATED ART

There have already been proposed disposable diapers provided in a front waist region as well as in a rear waist region with a plurality of elastic members circumferentially extending therein so that these elastic members may serve to improve a fit of the diaper to the wearer's body. For example, JP 2002-248127A cited herein discloses a disposable diaper comprising an absorbent structure extending across a crotch region and further extending into front and rear waist regions and a plurality of elastic members extending from transversely opposite side edges of the respective waist regions to at least outer side edges of the absorbent structure in a transverse direction.

PATENT DOCUMENT 1: JP 2002-248127A

DISCLOSURE OF THE INVENTION

Problem to be Solved by the Invention

The elastic members or the waist regions in the diaper disclosed by JP 2002-248127A comprise a plurality of elastic members circumferentially extending completely along respective waist-opening peripheries of the front and rear waist regions and a plurality of elastic members extending from the side edges of the respective waist regions to the side edges of the absorbent structure. In this way, a tensile stress of the waist elastic members is exerted on the side edges of the absorbent structure so as to improve a fit of the absorbent structure to the wearer's body.

According to the disclosure of JP 2002-248127A, the elastic members associated with the waist regions starting from the side edges of the respective waist regions do not extend across a central zone of the absorbent structure but terminate on lateral regions of the absorbent structure. Consequently, the tensile stress of these elastic members should not be directly exerted on the central zone of the absorbent structure and significantly affect the absorption capacity of the absorbent structure.

However, some of these elastic members associated with the waist regions circumferentially extend just above a pair of longitudinally opposite ends of the absorbent structure and the central zone of the absorbent structure should get wrinkled under contraction of these elastic members and the absorption capacity of the absorbent structure should be deteriorated. Obviously it may be contemplated to partially cut the elastic members extending above these ends of the absorbent structure or to partially remove these elastic members. However, according to such a countermeasure the regions in which none of the elastic members is present should drop down between the absorbent structure and the regions in which the elastic members are present in the course of putting the diaper on the wearer's body or during actual use of the diaper. It is also contemplated to provide these elastic members associated with the waist regions so as to be spaced from the absorbent structure by given distance. In this case also, such regions in which none of the elastic members is present should be spaced from the wearer's skin. In consequence, according to such a countermeasure, a feeling to wear the diaper should be deteriorated and the diaper should be displaced from the proper position.

The present invention on its first aspect provides a disposable diaper improved so that the liquid-absorbent structure can be put in close contact with the wearer's body in the front waist region without sacrificing the bodily fluid absorbing capacity of the liquid-absorbent structure while it is possible in the rear waist region to assure a space adapted to receive and retain discharged feces without anxiety of unintentionally spreading discharged feces and, in addition, an appropriate fit of the chassis as a whole to the wearer's body can be assured.

Measure to Solve the Problem

According to the present invention on its first aspect, there is provided a disposable diaper comprising:

a chassis having a longitudinal direction, a transverse direction, a side facing the wearer's skin and a side facing away from the wearer's skin and configurationally comprising a front waist region, a rear waist region, a crotch region extending between said front and rear waist regions, a waist-opening and a pair of leg-openings, a liquid-absorbent structure provided on the side facing the wearer's skin of the chassis and extending across the crotch region further into said front and rear waist regions, the liquid-absorbent structure containing therein a liquid-absorbent core, and, in each of the front and rear waist regions, the disposable diaper comprises an upper elasticized region extending in a vicinity of a periphery of the waist-opening, lower elasticized regions, an intermediate elasticized region extending between the upper elasticized region and the lower elasticized regions and outside longitudinally opposite ends of the liquid-absorbent structure, and a non-elasticized region.

According to the present invention is characterized in that at least in the front waist region of the front and rear waist regions, the non-elasticized region opposed to a central zone of the liquid-absorbent core wherein a tensile stress of the intermediate elasticized region is lower than a tensile stress of the upper elasticized region.

The present invention may be implemented also in preferred embodiments as follow:

(1) The intermediate elasticized region has a tensile stress lower than a tensile stress of the lower elasticized regions.

(2) The relationship of the tensile stress among the upper elasticized region, the intermediate elasticized region and the lower elasticized region can be represented by the upper elasticized region>the lower elasticized region>the intermediate elasticized region.

(3) The upper elasticized region exhibits a tensile stress in a range of about 1.0 to 3.0 N/25 mm at a state corresponding to about 80% of its maximum extended state, the lower elasticized region exhibits a tensile stress in a range of about 0.5 to 2.0 N/25 mm at a state corresponding to about 80% of its maximum stretched state and the intermediate elasticized region exhibits a tensile stress in a range of about 0.3 to 1.0 N/25 mm at a state corresponding to about 80% of its maximum stretched state.

(4) Tape fasteners for disposal of used diaper are attached to the intermediate elasticized region.

Effect of the Invention

According to the present invention, at least in the front waist region of the front and rear waist regions, none of the elastic members is present in the range opposed to the central zone of the liquid-absorbent core and consequently, the bodily fluid absorbing capacity of the liquid-absorbent core should not be deteriorated under contraction of the elastic members. The tensile stress of the intermediate elasticized region overlying the front and rear ends of the liquid-absorbent core is lower than those of the upper and lower elasticized regions and therefore the chassis as a whole maintains an appropriate fit without sacrificing the bodily fluid absorbing capacity of the liquid-absorbent core.

BRIEF DESCRIPTION OF THE DRAWINGS

FIG. 3 is an exploded perspective view of the diaper.

Figure 1:
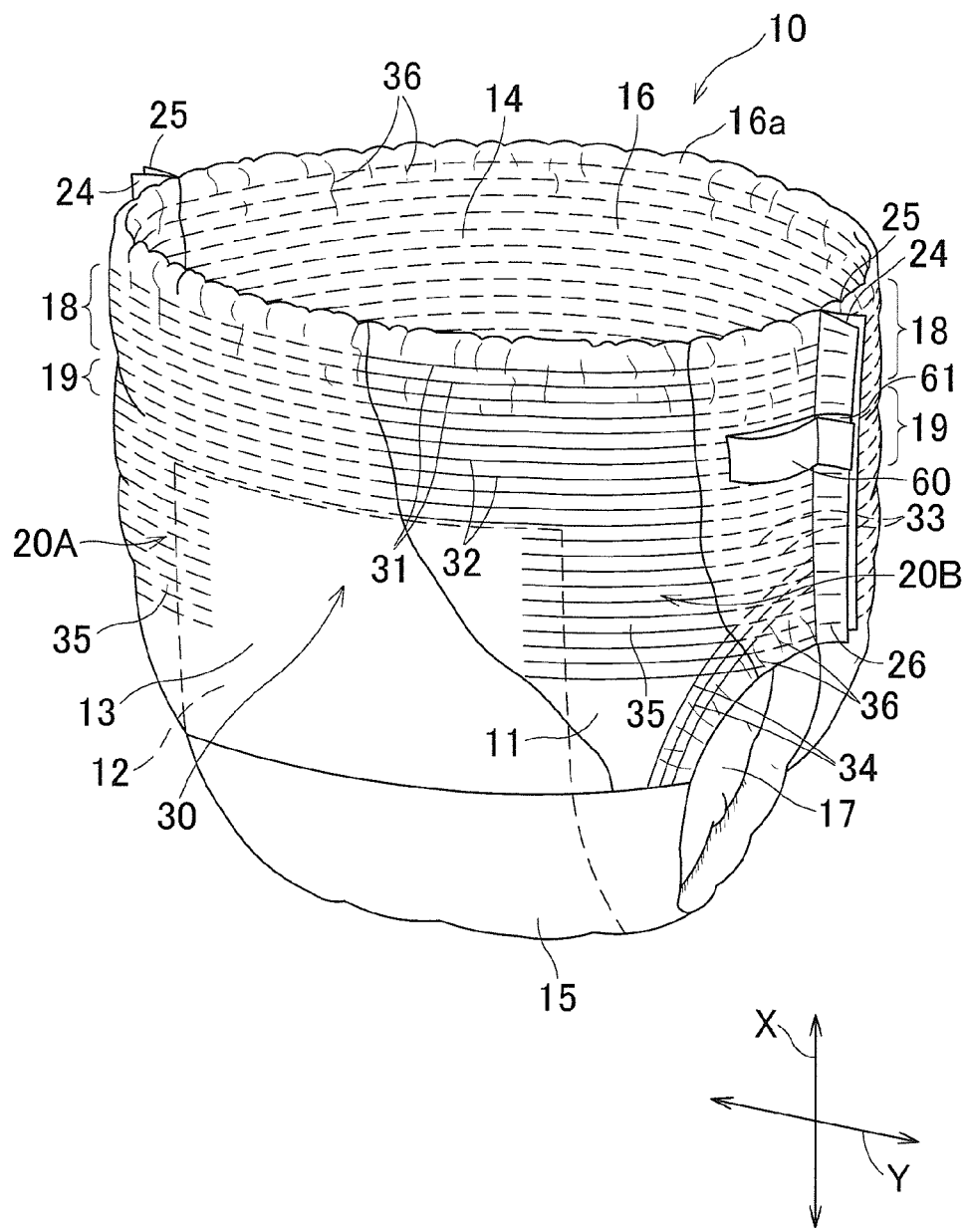
FIG. 1 is a partially cutaway perspective view of a diaper according to a first aspect of the invention as partially broken away.

IDENTIFICATION OF REFERENCE NUMERALS USED IN THE DRAWINGS 10 disposable diaper
11 chassis
12 liquid-absorbent structure
13 front waist region
14 rear waist region
15 crotch region
16 waist-opening
17 leg-openings
18 upper elasticized region
19 intermediate elasticized region
20A, 20B lower elasticized regions
24 side edges of front waist region
25 side edges of rear waist region
30 non-elasticized region
44 liquid-absorbent core
44d central zone of liquid-absorbent core
60 tape fastener for disposal of diaper
112 side edges of liquid-absorbent structure
X longitudinal direction
Y transverse direction

DESCRIPTION OF THE BEST MODE FOR WORKING OF THE INVENTION

FIGS. 1 through 4 illustrate a first embodiment of the present invention on its first aspect. FIG. 1 is a partially cutaway perspective view of a diaper 10 as put on the wearer's body. Referring to FIG. 1 showing the diaper 10 put on the wearer's body wherein a longitudinal direction is designated by X and a transverse direction is designated by Y.

As will be seen in FIG. 1, the diaper 10 comprises a chassis 11 and a liquid-absorbent structure 12 attached to the inner side of the chassis 11, i.e., the side of the chassis 11 facing the wearer's skin and extending in the longitudinal direction X. The diaper 10 configurationally comprises a front waist region 13, a rear waist region 14 and a crotch region 15 extending between these two waist regions. Each of the front and rear waist regions 13, 14 is sectionalized into an upper elasticized region 18, an intermediate elasticized region 19, lower elasticized regions 20A, 20B and a non-elasticized region 30 extending between the lower elasticized regions 20A, 20B. The upper elasticized region 18 is provided with a plurality of first waist elastic members 31 extending along a waist periphery 16a in the transverse direction Y, the lower elasticized regions 20A, 20B are respectively provided with a plurality of third waist elastic members 33 extending in the transverse direction Y across opposite lateral regions of each waist region 13 or 14, and the intermediate elasticized region 19 is provided with a plurality of waist elastic members 32 extending in the transverse direction Y between the first waist elastic members 31 and the third waist elastic members 33. As one variant, it is possible to form the non-elasticized region 30 in the front waist region 13 alone.

Figure 2:
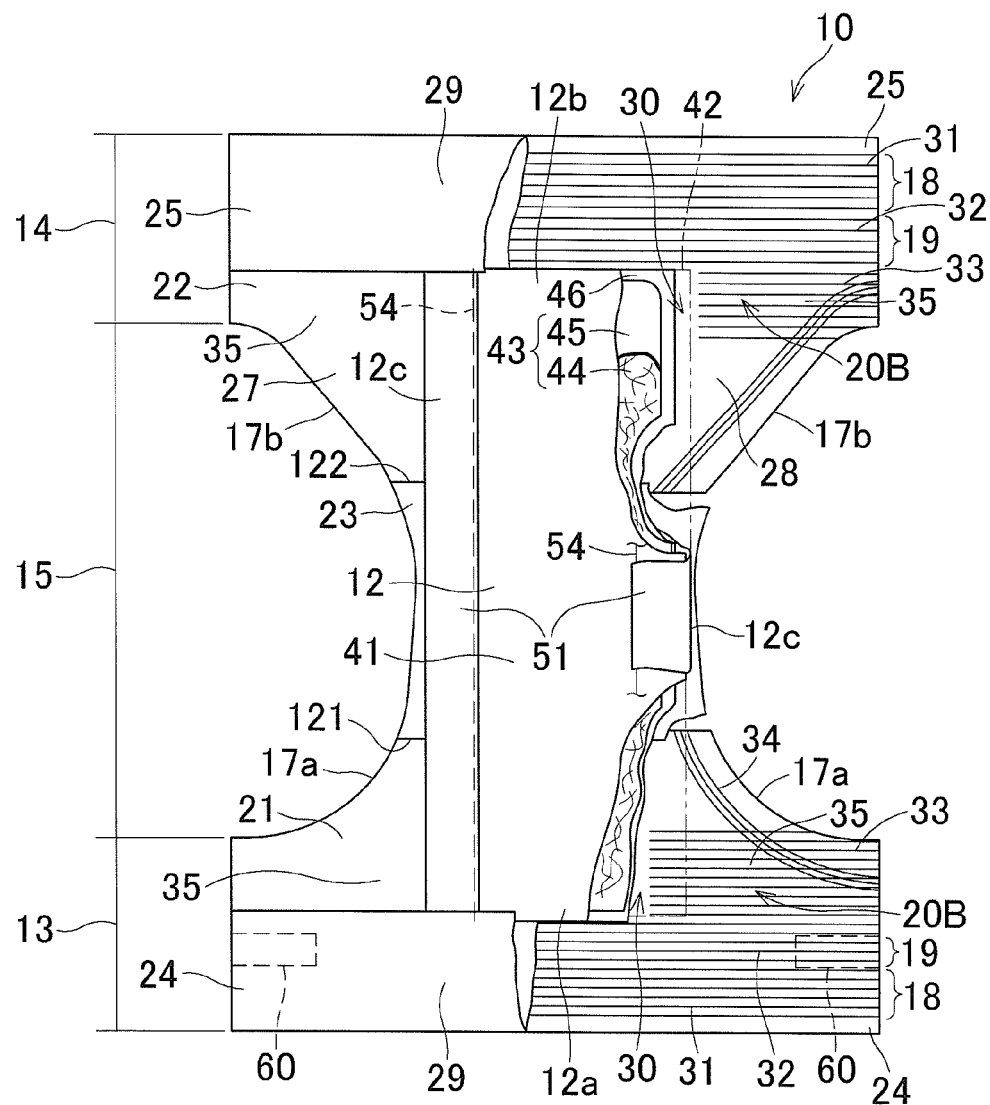
FIG. 2 is a developed plan view showing the diaper.

FIG. 2 is a developed plan view of the diaper 10 as the front and rear waist regions 13, 14 have been separated from each other along respective seams 26 and developed in the longitudinal direction X as well as in the transverse direction Y and FIG. 3 is an exploded perspective view of the diaper 10 as the chassis 11 and the liquid-absorbent structure 12 have been separated from each other.

The chassis 11 comprises a substantially trapezoidal front member 21 including the front waist region 13, a substantially trapezoidal rear member 22 including the rear waist region 14 and a substantially rectangular intermediate member 23 including the crotch region 15. These front member 21, intermediate member 23 and the rear member 22 are arranged in the longitudinal direction X in this order and joined together along joint lines 121, 122. Referring again to FIG. 1, respective pairs of transversely opposite side edges 24, of the front member 21 and the rear member 22 are put flat and bonded together at seams 26 arranged intermittently in the longitudinal direction X by means of, for example, hot melt adhesive, heat embossing, sonic or heat sealing technique, whereupon a waist-opening 16 and a pair of leg-openings 17 are defined. The transversely opposite side edges 24 are provided on the outer surface with tape fasteners 60 attached thereto. These tape fasteners are used to fasten the soiled diaper 10 in a rolled up state for disposal.

The front member 21, the intermediate member 23 and the rear member 22 are formed by a liquid-pervious inner layer sheet 27 facing the wearer's skin and a liquid-impervious outer layer sheet 28 facing away from the wearer's skin joined to each other. Both the inner layer sheet 27 and the outer layer sheet 28 are formed from an air-permeable fibrous nonwoven fabric. The outer layer sheet 28 extends in the longitudinal direction X beyond longitudinally opposite ends of the inner layer sheet 27. After the liquid-absorbent structure 12 has been placed on the inner side of the chassis 11, the portions 29 of the outer layer sheet 28 extending outward beyond the opposite ends of the inner layer sheet 27 in this manner are folded back toward the liquid-absorbent structure 12 so as to cover front and rear ends 12a, 12b of the liquid-absorbent structure 12 and bonded thereto at the respective pairs of side edges 24, 25 of the front and rear waist regions 13, 14. The portions 29 of the outer layer sheet 28 covering the front and rear ends 12a, 12b of the liquid-absorbent structure 12 from above function as leak-barrier walls preventing body waste from leaking out even if any amount of bodily fluids which has not been absorbed by the liquid-absorbent structure 12 leaks beyond the front and rear ends 12a, 12b.

Between the inner layer sheet 27 and the outer layer sheet 28, the first waist elastic members 31, the second waist elastic members 32, the third waist elastic members 33 and a plurality of leg elastic members 34 extending along upper and lower halves 17a, 17b of the respective leg-openings' peripheries are interposed. These elastic members 31, 32, 33, 34 are attached under tension at least to the inner layer sheet 27 of the inner layer sheet 27 and outer layer sheet 28 by means of hot melt adhesive (not shown). A plurality of gathers 36 appear in the chassis 11 under contraction of these elastic members 31, 32, 33, 34 (See FIG. 1).

The liquid-absorbent structure 12 has a substantially rectangular shape and comprises a liquid-pervious inner sheet 41, a liquid-impervious outer sheet 42 and a liquid-absorbent core assembly 43 interposed between these two sheets. The inner sheet 41 and the outer sheet 42 extend outward beyond a peripheral edge of the substantially rectangular core assembly 43 and the portions of these sheets 41, 42 extending outward beyond the periphery of the core assembly 43 are put flat and bonded together by means of hot melt adhesive (not shown) to define the front end 12a opposed to the front end of the chassis 11, the rear end 12b opposed to the rear end of the chassis 11 and a pair of opposite side edges 12c extending between the front and rear ends 12a, 12b in the longitudinal direction X. The front end 12a and the rear end 12b are bonded to the inner layer sheet 27 in the front member 21 and to the inner layer sheet 27 in the rear member 22, respectively, by means of hot melt adhesive (not shown).

The core assembly 43 comprises a rectangular liquid-absorbent core 44 formed from a mixture of fluff pulp, super-absorbent polymer particles and, if desired, heat-sealable staple fibers and a liquid-spreadable shape retaining sheet 45 such as tissue paper with which the core 44 is wrapped. Between the outer sheet 42 and the core assembly 43, a liquid-barrier sheet 46 formed from a liquid-impervious and moisture-permeable plastic film is interposed. A size of the liquid-barrier sheet 46 is sufficient to cover most part of the bottom face of the core assembly 43 and preferably covers the entire bottom face of the core assembly 43 in order to ensure a sufficient leak-barrier effect.

A pair of barrier cuffs 51 each formed from a liquid-impervious sheet and extending in the longitudinal direction X are attached to the opposite side edges 12c of the liquid-absorbent structure 12. Each of these barrier cuffs 51 has a fixed edge 52 fixed between the associated side edge 12c of the liquid-absorbent structure 12 and the chassis 11 so as to intersect with the innermost segment of the associated leg elastic members 34 and a free edge 53 collapsed toward the side of the liquid-absorbent core 44 wherein at least a single elastic member 54 extending in the longitudinal direction X is attached to the inner surface of the free edge 53. With the diaper 10 put on the wearer's body, the free edge 53 is spaced upward from the inner sheet 41 under contraction of the elastic member 54 and thereby completely covers the associated side edge 12c of the liquid-absorbent structure 12 to prevent any amount of body waste from leaking sideways. In the crotch region 15, the elastic member 54 extends in the longitudinal direction X and cooperates with the leg elastic members 34 extending along the upper and lower halves 17a, 17b of the associated leg-opening 17 to define an imaginary annular elasticized region along this leg-opening 17. In this way, the imaginary annular elasticized regions surround the wearer's legs (not shown) and thereby prevent leak of body waste from occurring around the wearer's legs.

Figure 4A:
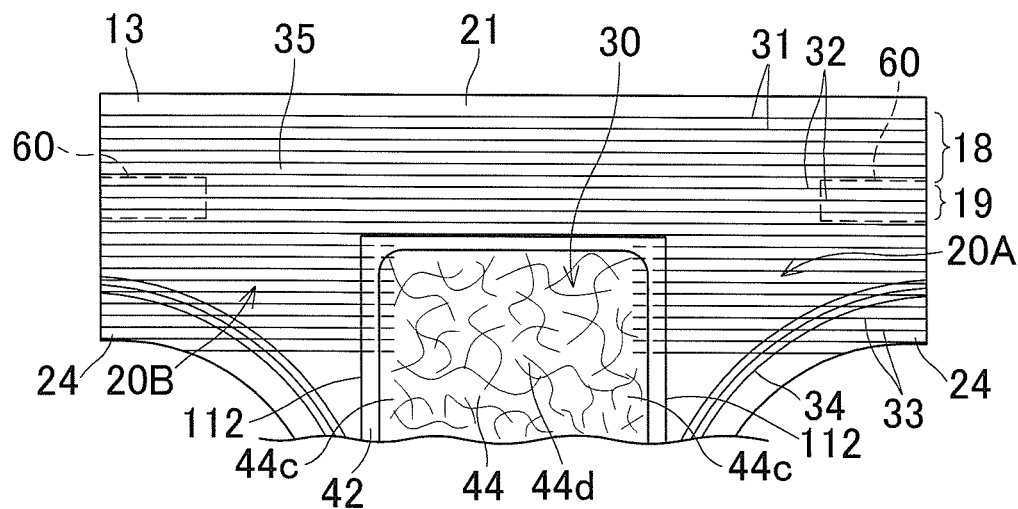
FIG. 4 shows a front member of the diaper in a partially scale-enlarged view A and a rear member of the diaper in a partially scale-enlarged view B.
Figure 4B:
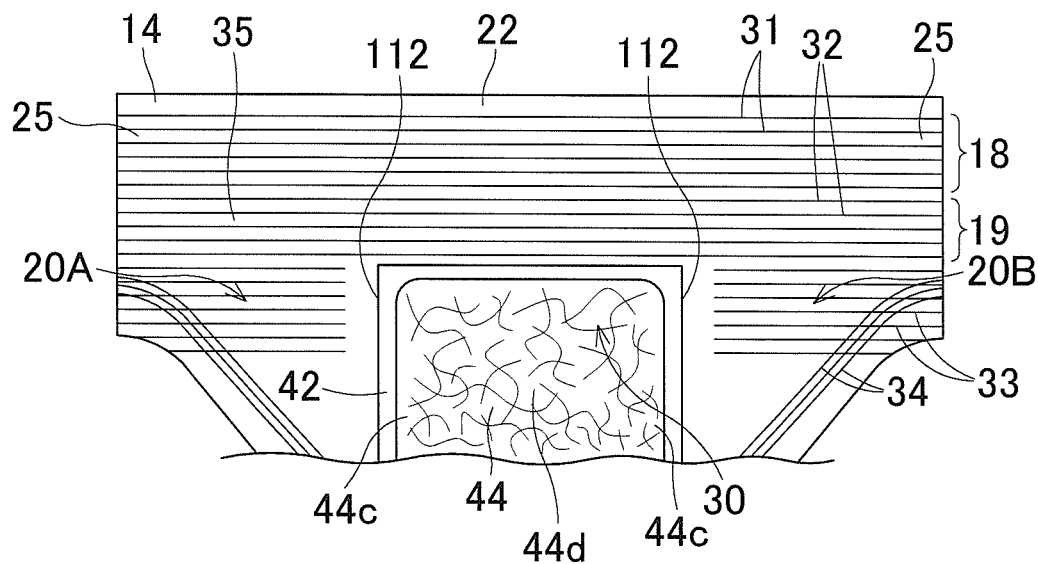

FIGS. 4A and 4B are partially scale-enlarged diagrams illustrating the front member 21 and the rear member 22, respectively. For convenience of illustration, the inner layer sheet 27, the liquid-barrier sheet 46, the shape retaining sheet 45 and the inner sheet 41 are eliminated in FIGS. 4A and 4B.

In the front waist region 13, as will be apparent from FIGS. 4A and 4B, the third waist elastic members 33 extend from the opposite side edges 24 in the transverse direction slightly beyond the opposite side edges 112 of the liquid-absorbent structure 12 to opposite side edges 44c of the liquid-absorbent core assembly 44 and not into the central zone 44d. In the rear waist region 14, the third waist elastic members 33 extend from the opposite side edges 25 and terminate short of the opposite side edges 112 of the liquid-absorbent structure 12.

To assure a desired fit of the liquid-absorbent structure 12 to the wearer's body in the front waist region 13, it is essential that the lower elasticized regions 20A, 20B including the third waist elastic members 33 extending therein should have a correspondingly high tensile stress. However, the intermediate elasticized regions 19 overlying these lower elasticized regions 20A, 20B and including the second waist elastic members 32 extending therein preferably has a tensile stress lower than the tensile stress of the lower elasticized regions 20A, 20B. Specifically, to minimize any affection due to contraction of the waist elastic members 31, 32, 33 exerted on the core 44 and thereby to maintain the desired body fluid absorbing capacity of the core 44, it may be contemplated that the second waist elastic members 32 extending outside the front and rear ends 12a, 12b of the liquid-absorbent structure 12 as viewed in the longitudinal direction X, i.e., extending in the intermediate elasticized region 19 are spaced from the front and rear ends of the liquid-absorbent core 44 by an appropriate distance or the tensile stress of the second elastic members 32 themselves is appropriately reduced. However, if the second waist elastic members are eliminated or spaced in the longitudinal direction X from the liquid-absorbent structure 12 by a given distance, both the front waist region 13 and the rear waist region 14 will be formed with relatively large non-elasticized regions, undesirably resulting in a deteriorated fit of the chassis 11. It may be also contemplated that the intermediate region 19 is provided with the second waist elastic members 32 and these elastic members 32 are partially cut off or removed at locations above the front end 12a of the liquid-absorbent structure 12. However, such measure is inevitably accompanied with an inconvenience, for example, when the waist-opening periphery 16a is pulled up in the course of putting the diaper 10 on the wearer's body, the non-elasticized region including none of the second waist elastic members 32 extending therein stays at its initial level without being pulled up together with the upper elasticized region 18 and the lower elasticized regions 20A, 20B to a desired level. In consequence, this non-elasticized region dropped down between the upper elasticized region 18 and the liquid-absorbent structure 12, affecting not only the feeling to wear but also the appearance. In addition, if bodily fluids are discharged directly onto such dropped down region, such bodily fluids should not be completely absorbed by the liquid-absorbent core and any amount thereof should eventually leak out.

According to the present invention on its first aspect, the intermediate elasticized region 19 including the second waist elastic members 32 extending therein is formed above the front and rear ends 12a, 12b of the liquid-absorbent structure 12 in a manner that the tensile stress of this intermediate elasticized region 19 is adjusted not to affect the liquid absorbing capacity of the liquid-absorbent core 44. In this way, both requirements for the bodily fluid absorbing capacity and the appropriate fitness of the diaper 10 can be satisfied.

To assure a desired fit of the liquid-absorbent structure to the wearer's body, it is required for the lower elasticized regions 20A, 20B to have the correspondingly desired tensile stress. To stabilize the front and rear waist regions 13, 14 of the diaper 10 at desired waist regions of the wearer's body, it is required for the upper elasticized region 18 extending in the transverse direction Y along the waist-opening periphery 16a to have a tensile stress higher than those of the intermediate elasticized region 19 and the lower elasticized regions 20A, 20B. In other words, the respective tensile stress values of the upper elasticized region 18 and the lower elasticized regions 20A, 20B are preferably higher than at least the tensile stress of the intermediate elasticized region 19. More specifically, the upper elasticized region 18, the intermediate elasticized region 19 and the lower elasticized regions 20A, 20B preferably have respective tensile stress values as measured in the transverse direction X in a mutual relationship expressed by the upper elasticized region 18>the lower elasticized regions 20A, 20B>the intermediate elasticized region 19.

Specifically, in the preferable mutual relationship among the respective elasticized regions, the upper elasticized region 18 should exhibit a tensile stress in a range of about 1.0 to 3.0 N/25 mm at the state corresponding to about 80% of its maximum stretched state, the lower elasticized regions 20A, 20B should exhibit a tensile stress in a range of 0.5 to 2.0 N/25 mm at the state corresponding to about 80% of its maximum stretched state and the intermediate elasticized region 19 should exhibit a tensile stress in a range of about 0.3 to 1.0 N/25 mm at the state corresponding to about 80% of its maximum stretched state. Particularly, if the tensile stress of the intermediate elasticized region 19 is less than about 0.3 N/25 mm, the intermediate elasticized region 19 should drop down between the upper elasticized region 18 and the liquid-absorbent structure 12 as has previously been described.

As has previously been described, the waist elastic members 31, 32, 33 are permanently bonded, under respective tensions given by predetermined extending ratios in the transverse direction Y, to at least to the inner surface of the inner layer sheet 27. Preferably, in the course of bonding these elastic members to the inner layer sheet 27, the first waist elastic members 31 are under a tension given by the extending ratio in a range of about 200 to 350%, the second waist elastic members 32 are under a tension given by the extending ratio in a range of about 160 to 250% and the third waist elastic members 33 are under a tension given by the extending ratio in a range of about 250 to 400%. If the first waist-surrounding elastic members 31 are attached, under a tension given by the extending ratio less than about 200%, to the inner layer sheet 27, it will be difficult to broaden the waist-opening 16 sufficiently to receive the wearer's legs smoothly even if it is tried to pull the waist-opening periphery 16a in the transverse direction Y when the diaper 10 is put on the wearer's body. Practically in consequence, it is difficult to put the diaper 10 on the wearer's body. The second waist elastic members 32 are preferably attached to the inner layer sheet 27 under a tension given by the extending ratio as low as possible in order to prevent the liquid-absorbent core 44 from being unacceptably contracted. However, if the extending ratio is less than 160%, the desired fit of the intermediate elasticized region 19 to the wearer's body can no more assured and eventually the intermediate elasticized region 19 as a whole should slip down between the upper elasticized region 18 and the liquid-absorbent structure 12.

As will be appreciated from the foregoing description, the extending ratio of the third elastic members 33 may be set to be higher than those of the first and second waist elastic members 31, 32 to ensure that the lower elasticized regions 20A, 20B can be extended depending on the wearer's body shape and in response to the wearer's movement and thereby any significant displacement of the liquid-absorbent structure 12 can be avoided.

The tape fasteners 60 for disposal of the used diaper are preferably attached to the front and rear waist regions 13, 14 in the respective intermediate elasticized regions 19. As has previously been described, the intermediate elasticized region 19 has the tensile stress and the extending ratio both lower than those of the other elasticized regions 18, 20A, 20B and, therefore, fixed regions 61 of the respective tape fasteners are substantially free from contraction of the other regions. In consequence, operation of fastening the used diaper 10 can be smoothly carried out for disposal thereof.

The first waist elastic members 31, the second and third waist members 32, 33 maybe made of natural or synthetic rubber and may be implemented in the form of strings, cords or tape having rubber elasticity such as, Lycra (Registered Trademark) as elastic elements. In the case of the illustrated example, in the front waist region 13, the first waist elastic member 31 comprises six elastic elements, the second waist elastic member 32 comprises three elastic elements and the third waist elastic member 33 comprises twelve elastic elements. In the rear waist region 14, the first waist elastic member 31 comprises six elastic elements, the second waist elastic member 32 comprises five elastic elements and the third elastic member 33 comprises seven elastic elements. The number of these elastic elements as well as a distance between each pair of the adjacent elastic elements in the respective elastic members may be appropriately varied depending on the tensile stress and the extending ratio required for the respective elasticized regions 18, 19, 20A, 20B. The lower elasticized regions 20A, 20B in the front waist region 13 preferably have a tensile stress higher than that of the lower elasticized regions 20A, 20B in the rear waist region 14. This is for the reason that, in the front waist region 13, the liquid-absorbent structure 12 must be held in close contact with the wearer's body to prevent urine leak while, in the rear waist region 14, it is essential to assure the space serving to retain discharged feces and the fit may be of a degree sufficient to prevent urine leakage.

While the first waist elastic members 31, the second and third waist elastic members 32, 33 are attached to the respective regions 18, 19, 20A, 20B to elasticize these regions in the illustrated embodiment, it is possible to form the respective elasticized regions 18, 19, 20A, 20B by sheet members themselves having elasticity or by permanently attaching such elastic sheets to the inner surface of the chassis 11.

The tensile stress values of the respective elasticized regions 18, 19, 20A, 20B are measured by a method as will be described below.

First, the diaper 10 is developed as seen in FIG. 2 and the respective waist elastic members 31, 32, 33 are extended. Test pieces each having a width of about 25 mm for the respective elasticized regions 18, 19, 20A, 20B are cut away from the diaper 10 in this extended state and this length of about 25 mm is the maximum extended length. The test piece is held by chucks of a contractile strength tester and subjected to 1 cycle test with a moving velocity of 100 mm/min and an inversion distance corresponding to 90% of the maximum extended length of the test piece. A tensile stress after inversion is measured at a point the length of the test piece reaching 80% of its maximum extended length. It should be noted that a distance between the chucks should be appropriately changed depending on the test piece and, when it is difficult to obtain the test piece having a width of 25 mm, the measurement may be carried out on the basis of the test piece having an optional width and the measurement result may be converted into a tensile stress value to be obtained on the basis of the test piece having a width of 25 mm.

The components constituting the diaper 10 of the invention such as the inner and outer layer sheets 27, 28, the inner and outer sheets 41, 42 and the liquid-absorbent structure 12 may be formed by those conventionally used in the relevant field used to make the disposable diaper. While the pants-type disposable diaper 10 comprising the front and rear waist regions joined together along the respective pairs of opposite side edges 24, 25 are illustrated and described as the embodiment, the present invention is applicable not only to the pants-type diaper but also to the open-type diaper. It is also possible to form the front member 21 and the intermediate member 23 of the chassis 11 by a continuous sheet or to form the chassis 11 by the front member 21 and the rear member 22 without incorporation of the intermediate member 23.

The invention claimed is:

1. A disposable diaper comprising:
  a chassis having a longitudinal direction, a transverse direction, a side facing the wearer's skin and a side facing away from the wearer's skin and configurationally comprising a front waist region, a rear waist region, a crotch region extending between said front and rear waist regions, a waist-opening and a pair of leg-openings,
  a liquid-absorbent structure provided on said side facing the wearer's skin of said chassis and extending across said crotch region further into said front and rear waist regions, said liquid-absorbent structure containing therein a liquid-absorbent core, and,
  each of said front and rear waist regions comprising an upper elasticized region extending in the transverse direction along a periphery of said waist-opening,
  a pair of lower elasticized regions spaced apart from each other in the transverse direction and disposed in opposite lateral regions of each waist region,
  a non-elasticized region disposed between said pair of lower elasticized regions and opposed to a central zone of said liquid-absorbent structure, and
  an intermediate elasticized region extending between the upper elasticized region and the lower elasticized regions and outside of longitudinally opposite ends of the liquid-absorbent structure,
  wherein in at least in the front waist region of the front and rear waist regions a tensile stress of the intermediate elasticized region is lower than a tensile stress of the upper elasticized region.

2. The diaper according to claim 1, wherein said intermediate elasticized region has a tensile stress lower than a tensile stress of said lower elasticized regions.

3. The diaper according to claim 1, wherein a relationship of said tensile stress among the upper elasticized region, said intermediate elasticized region and said lower elasticized region can be represented by said upper elasticized region>the lower elasticized region>said intermediate elasticized region.

4. The diaper according to claim 1, wherein said upper elasticized region exhibits a tensile stress in a range of about 1.0 to 3.0 N/25 mm at a state corresponding to about 80% of its maximum extended state, said lower elasticized region exhibits a tensile stress in a range of about 0.5 to 2.0 N/25 mm at a state corresponding to about 80% of its maximum stretched state and said intermediate elasticized region exhibits a tensile stress in a range of about 0.3 to 1.0 N/25 mm at a state corresponding to about 80% of its maximum stretched state.

5. The diaper according to claim 1, wherein tape fasteners for disposal of used diaper are attached to said intermediate elasticized region.

6. The diaper according to claim 2, wherein a relationship of said tensile stress among the upper elasticized region, said intermediate elasticized region and said lower elasticized region can be represented by said upper elasticized region>the lower elasticized region>said intermediate elasticized region.

7. The diaper according to claim 2, said upper elasticized region exhibits a tensile stress in a range of about 1.0 to 3.0 N/25 mm at a state corresponding to about 80% of its maximum extended state, said lower elasticized region exhibits a tensile stress in a range of about 0.5 to 2.0 N/25 mm at a state corresponding to about 80% of its maximum stretched state and said intermediate elasticized region exhibits a tensile stress in a range of about 0.3 to 1.0 N/25 mm at a state corresponding to about 80% of its maximum stretched state.

8. The diaper according to claim 3, said upper elasticized region exhibits a tensile stress in a range of about 1.0 to 3.0 N/25 mm at a state corresponding to about 80% of its maximum extended state, said lower elasticized region exhibits a tensile stress in a range of about 0.5 to 2.0 N/25 mm at a state corresponding to about 80% of its maximum stretched state and said intermediate elasticized region exhibits a tensile stress in a range of about 0.3 to 1.0 N/25 mm at a state corresponding to about 80% of its maximum stretched state.

9. The diaper according to claim 6, said upper elasticized region exhibits a tensile stress in a range of about 1.0 to 3.0 N/25 mm at a state corresponding to about 80% of its maximum extended state, said lower elasticized region exhibits a tensile stress in a range of about 0.5 to 2.0 N/25 mm at a state corresponding to about 80% of its maximum stretched state and said intermediate elasticized region exhibits a tensile stress in a range of about 0.3 to 1.0 N/25 mm at a state corresponding to about 80% of its maximum stretched state.

10. The diaper according to claim 2, wherein tape fasteners for disposal of used diaper are attached to said intermediate elasticized region.

11. The diaper according to claim 3, wherein tape fasteners for disposal of used diaper are attached to said intermediate elasticized region.

12. The diaper according to claim 4, wherein tape fasteners for disposal of used diaper are attached to said intermediate elasticized region.

13. The diaper according to claim 6, wherein tape fasteners for disposal of used diaper are attached to said intermediate elasticized region.

14. The diaper according to claim 7, wherein tape fasteners for disposal of used diaper are attached to said intermediate elasticized region.

15. The diaper according to claim 8, wherein tape fasteners for disposal of used diaper are attached to said intermediate elasticized region.

16. The diaper according to claim 9, wherein tape fasteners for disposal of used diaper are attached to said intermediate elasticized region.

* * * * *

UNITED STATES PATENT AND TRADEMARK OFFICE
CERTIFICATE OF CORRECTION

PATENT NO. : 8,915,900 B2  
APPLICATION NO. : 12/742729  
DATED : December 23, 2014  
INVENTOR(S) : Shimada et al.

Page 1 of 1

It is certified that error appears in the above-identified patent and that said Letters Patent is hereby corrected as shown below:

In the Specification

Under the Related Application section, Column 1, line 6, delete "PCT/JP2008/064596" and substitute --PCT/JP2008/064595-- in its place.

Signed and Sealed this
Twenty-seventh Day of October, 2015

Michelle K. Lee
*Director of the United States Patent and Trademark Office*